(12) United States Patent
Renner

(10) Patent No.: US 8,198,584 B2
(45) Date of Patent: Jun. 12, 2012

(54) MEASUREMENT OF ION MOBILITY SPECTRA WITH ANALOG MODULATION

(75) Inventor: Uwe Renner, Leipzig (DE)

(73) Assignee: Bruker Daltonik GmbH, Breman (DE)

( * ) Notice: Subject to any disclaimer, the term of this patent is extended or adjusted under 35 U.S.C. 154(b) by 135 days.

(21) Appl. No.: 12/816,796

(22) Filed: Jun. 16, 2010

(65) Prior Publication Data

US 2010/0320375 A1    Dec. 23, 2010

(30) Foreign Application Priority Data

Jun. 22, 2009  (DE) .......................... 10 2009 025 727

(51) Int. Cl.
*H01J 49/40*  (2006.01)
*B01D 59/44*  (2006.01)
(52) U.S. Cl. .................. 250/287; 250/286; 250/282
(58) Field of Classification Search .......... 250/281–282, 250/286–287
See application file for complete search history.

(56) References Cited

U.S. PATENT DOCUMENTS

| | | | |
|---|---|---|---|
| 4,633,083 A | 12/1986 | Knorr et al. | |
| 4,707,602 A * | 11/1987 | Knorr | 250/282 |
| 5,396,065 A | 3/1995 | Myerholtz et al. | |
| 5,719,392 A | 2/1998 | Franzen | |
| 6,198,096 B1 | 3/2001 | Le Cocq | |
| 6,580,068 B1 | 6/2003 | Tarver, III et al. | |
| 6,782,342 B2 | 8/2004 | LeGore et al. | |
| 7,417,222 B1 | 8/2008 | Pfeifer et al. | |
| 8,022,359 B2 * | 9/2011 | Michelmann | 250/282 |
| 2004/0144918 A1 * | 7/2004 | Zare et al. | 250/287 |
| 2009/0236514 A1 * | 9/2009 | Renner | 250/282 |
| 2009/0294647 A1 | 12/2009 | Michelmann | |

FOREIGN PATENT DOCUMENTS

WO    2004102178    11/2004

OTHER PUBLICATIONS

Knorr et al., "Fourier Transform Ion Mobility Spectrometry", Anal. Chem. 1985, col. 57, pp. 406-406.

* cited by examiner

*Primary Examiner* — Jack Berman
*Assistant Examiner* — David E Smith
(74) *Attorney, Agent, or Firm* — O'Shea Getz P.C.

(57) ABSTRACT

A method is provided for measuring mobility spectrum of ions in an ion mobility spectrometer having an ion source, a modulator, an ion drift region and an ion detector disposed at the end of the ion drift region. The method includes the steps of modulating an ion current from the ion source, and measuring the mobility spectrum, where a predistortion of the continuous modulation function substantially compensates for a distortion created by the modulator. The ion current is modulated with the modulator by varying an instantaneous frequency of a continuous modulation function across a frequency range. The mobility spectrum is measured by correlating the ion current measured at the detector and the modulation function.

11 Claims, 2 Drawing Sheets

MEASUREMENT OF ION MOBILITY SPECTRA WITH ANALOG MODULATION

CROSS-REFERENCE INFORMATION

This patent application is related to U.S. patent application Ser. No. 12/407,511 filed on Mar. 19, 2009, which is hereby incorporated by reference.

PRIORITY INFORMATION

This patent application claims priority from German patent application 10 2009 025 727.6 filed on Jun. 22, 2009, which is hereby incorporated by reference.

FIELD OF THE INVENTION

The invention relates to a method for measuring ion mobility spectra using an ion mobility spectrometer (IMS).

BACKGROUND OF THE INVENTION

Ion mobility spectrometers (IMS) measure mobility of ions in gases influenced by an electric drawing field. The mobility of an ion can provide information on its size and shape. Mobility spectrum can identify the ionized substances in the spectrometers such that trace pollutants, for example, can be measured.

During operation of a typical ion mobility spectrometer, ions are continuously generated in short pulses by an ion source and introduced into a drift region of the spectrometer via a gating grid. The gating grid can be a fine bipolar grid such as a Bradbury-Nielsen grid. The introduction pulse periods usually last between 150 and 300 microseconds, and the recording of the spectrum takes about 30 milliseconds. The ion packets transmitted through the grid by the pulses are pulled through a collision gas in the drift region by an axial electric field. The measured mobility of the ions is used to determine velocities of the ions, which, as known in the art, depend on their collision cross-section, their mass, their charge, their ability to become polarized and their tendency to form complex ions with molecules from the collision gas.

Ion species such as monomers, dimers, trimers, doubly charged monomers and complexes with water and collision gas molecules are typically formed in the ion source from molecules of a gas (e.g., air) introduced into the spectrometer. Every ion species has a characteristic mobility. At the end of the drift region, incident ion current is measured with the ion detector and digitized as a drift time spectrum or "mobility spectrum". The mobility spectrum is then stored as a digitized sequence of measured ion current values. The mobility spectra are typically summed over one or even several seconds to determine a sum spectrum with relatively little noise. The summation period can also be shorter than one second where, for example, the dynamic behavior of chemical reactions under changing concentrations is being detected.

Evaluating the mobility spectrum can provide information on the mobility of the ions as well as information on the formation of dimers and doubly charged ions. This information can in turn indicate the identity of the substances in the gas introduced into the spectrometer. Additional information regarding the identity of the substances can be determined by acquiring a series of mobility spectra under variation of the concentration of the substance, as they occur naturally when substances appear or vanish in the air. Changes of the signal intensity ratios of dimer ions to monomer ions or doubly to singly charged ions can provide additional information regarding the identity of the substances and substance concentrations within the gas.

An ion mobility spectrometer may be used to detect, for example, explosives or drugs in suitcases/baggage at an airport. In this example, the suitcases are swabbed. The swab spot on the swab material is heated close to the inlet of the mobility spectrometer such that a cloud of vaporized substance enters the ion source of the spectrometer. The concentration increases rapidly in about a second and drops again in five to ten seconds. Initially the signal of the monomer ions increases, but is soon overtaken by that of the dimer ions, after which trimer ions can appear. The temporal behavior of the ion ratios is characteristic of the vaporized substances and provides additional identification information, which can reduce the rate of false alarms (i.e., false positives). Approximately five to ten mobility spectra per second must be acquired to measure the dynamic characteristics, which requires a method with a relatively high signal-to-noise ratio.

Approximately between one half a percent and one percent of the ions of the gaseous substance introduced into the spectrometer are utilized for a conventional spectrum measurement repetition rate of about 30 spectra per second, and an ion transmission time of between 150 and 300 microseconds. The remaining ions are discharged, for example at the gating grid, and are thereby lost to the measurement process. Notably, by increasing the percentage of the ions utilized from one percent to 50 percent, the signal-to-noise ratio can be improved by a factor of $\sqrt{(50)} \approx 7$.

U.S. Patent Application Publication No. 2009/0236514 A1 to Uwe Renner, which is hereby incorporated by reference, discloses a method for analog modulating the ion current from the ion source with a continuous modulation function. The continuous modulation function has an instantaneous frequency varying over a wide frequency range. The resulting ion current signal at the detector is decoded by a correlation with the modulation function, which provides a relatively noise-free mobility spectrum with relatively good mobility resolution. A "chirp" is preferably used as the modulation function. The chirp is a sine wave type function, for example, whose instantaneous frequency increases from zero to an upper limit of a few kilohertz.

The modulation frequency is preferably varied as a single chirp that is extended over the chosen measuring time T. The chirp frequency is varied from a lower frequency limit of zero hertz (Hz) to an upper frequency limit v. The upper frequency limit determines the maximum mobility resolution. An upper frequency limit of seven kilohertz, for example, provides peak widths at one half the maximum height of about 200 microseconds. Preferably a "linear chirp" is used whose frequency increases linearly in time t. Such a linear chirp has the form $f(t) = a + b \sin(\pi v\, t^2/T)$, where $0 \leq t \leq T$.

The modulation control signal for the gating grid is generated by a digital-to-analog (D/A) conversion of previously calculated and stored values of the modulation function. The conversion rates of the digital-to-analog conversion of the modulation control signal, and also the analog-to-digital conversion of the ion current from the detector, should be relatively fast (e.g., at least five times the upper frequency limit). The bandwidth of the amplification and the bit resolution for the digital conversion should be higher than the bandwidth for a pulse-operated ion mobility spectrometer, because the ion currents with different frequency components can be superimposed on one another. The bandwidth, however, should not reach the saturation limit of the electronics.

On average, 50% of the ions are transmitted where the modulation has symmetrical control. Substantially all of these transmitted ions contribute to the generation of the mobility spectrum at full modulation depth between zero and one hundred percent of the ion current. Fifty percent of the ions therefore are utilized during the measurement. The variation of the modulation frequency in the chirp preferably starts at zero hertz and ranges up to about seven kilohertz for a typical spectrometer with a 10 centimeter drift length. This modulation affects all ion species. The patterns applied to the individual ion species move along with different drift speeds as the ions drift through the drift tube of the mobility spectrometer, such that the ion current at the ion detector exhibits a complicated pattern of superimpositions. The temporal sequence of the ion current is measured at the end of the drift region, digitized and stored. The stored signal pattern is decoded by a correlation with the modulation function, and the mobility spectrum of the ions therefore can be determined. The measurement is synchronized in time with the output of the modulation control signal.

The afore-described method has a tendency to generate single side bands of intense mobility signals in the mobility spectrum when typical gating grids are used as the modulators. In particular, the shorter the measuring time T chosen for a mobility spectrum, the stronger the formation of the side bands. Experiments and simulations have shown that these side bands are generated by a weak nonlinear modulation characteristic of the gating grid used as the modulator. The term "nonlinear" relates to the modulation of the ion current amplitude, and not to the increase in frequency of the chirp.

Disadvantageously, the side bands can imitate mobility signals of other ions. The side bands imitate signals of substances with low concentration, although they are broader than normal mobility signals. They complicate the evaluation of the mobility spectra, particularly when the dynamic characteristic is also to be measured by using short spectrum acquisition times.

FIG. 2 illustrates the measured transmission characteristic of the gating grid for the ion current in picoamperes (ordinate) as a function of the control voltage in volts (abscissa). The transmission characteristic has a broad linear operating range which appears, at first glance, suitable for a modulation. A more detailed analysis, however, shows a weak nonlinearity in the apparently linear region, which is shown by the curves of the two saturation regions merging slightly differently into the central linear region of the curve. This weak nonlinearity, which can be shown in mathematical simulations, can create side bands having strong mobility signals. These slight nonlinearities can also be created in spectrometers that use other types of grids.

What is needed therefore is an ion mobility spectrometer that can compensate for nonlinearities.

SUMMARY OF THE INVENTION

According to a first aspect of the present invention, a method is provided for measuring mobility spectrum of ions in an ion mobility spectrometer having an ion source, a modulator, an ion drift region and an ion detector disposed at the end of the ion drift region. The method includes the steps of modulating an ion current from the ion source, and measuring the mobility spectrum, where a predistortion of the continuous modulation function substantially compensates for a distortion created by the modulator. The ion current is modulated with the modulator by varying an instantaneous frequency of a continuous modulation function across a frequency range. The mobility spectrum is measured by correlating the ion current measured at the detector and the modulation function.

In one embodiment, a stream of air having, for example, small traces of water and substances to be analyzed enters the ion source housing. Some air molecules are ionized by the electrons of the beta emitter, which comprise for example $^{63}$Ni, and react in a complex way with water molecules to form complex ions (e.g., $(H_2O)_n.OH_3^+$ or $(H_2O)_n.OH^-$). The complex ions function as reactant gas ions for the ionization of the substance molecules to be detected. The ions in the ion source drift towards the gating grid where the ion current is analog modulated with the modulation function. The drift region includes electrodes separated by insulators. The electrodes are supplied with potentials via a voltage divider that includes individual resistors, where the potentials generate a uniform electric field in the drift region. The ions are pulled by this field through the drift region to a plane Faraday collector. The ion current is measured by the Faraday collector and provides a sequence of digital ion current values.

A signal distortion caused by a gating grid may be compensated using a corresponding predistortion of an ideal modulation function such that an apparently undistorted grid modulation is generated. For example, where the gating grid has a slight curvature of the transmission curve, a modulation function such as a chirp can be superimposed with a portion of a squared modulation function. The superposition causes the modulation function to become slightly asymmetric such that the asymmetry of the modulation caused by the small curvature can be compensated. The ion current signal produced is decoded at the detector, for example, by a correlation with the undistorted modulation function.

These and other objects, features and advantages of the present invention will become more apparent in light of the following detailed description of preferred embodiments thereof, as illustrated in the accompanying drawings.

DETAILED DESCRIPTION OF THE INVENTION

An ion current from an ion source may be modulated using a predistorted modulation function in a mobility spectrometer with a distorting modulator, such as a conventional gating grid, to provide a relatively undistorted ion current. The predistorted modulation function compensates the distortion of the modulator. The ion current signal produced at the detector is decoded by a correlation with the undistorted modulation function. Alternatively, the ion current signal may be decoded using the predistorted modulation function. Applying the distortion function that is inverse to the distortion by the gating grid generates a mobility spectrum (see FIG. 4) that does not include side bands of the strong mobility signals even with short measuring times of 100 ms. The modulation function may be, for example, a linear or nonlinear chirp.

Typical communication technologies use ion current amplitude modulation to modulate amplitude, frequency or (less often) phase of a high frequency carrier signal with a communication signal. The communication signal is included in amplitude variations, in frequency variations or (usually for digital communication signals) in phase jumps. In contrast, the substantially constant ion current which is modulated using the disclosed method originally has neither phase nor frequency; only the modulation function which modulates the ion current intensities between, for example, zero and full current intensity, is characterized by phases and frequencies. The modulation function which actually corresponds to the communication signal of communication technology is a coding that allows the partial ion currents of different ion mobilities included in the ion current to be identified via the modulation pattern.

A method of signal pre-distortion has recently been developed in mobile amplifier technology where amplifiers can operate nonlinearly to obtain undistorted amplifier output signals. In contrast to the present invention, however, this signal pre-distortion method distorts a signal to be amplified, and not a modulation function that modulates the signal. In particular, the signal predistortions are applied digitally to the digital output signals before being converted into analog signals. For example, when playing digitally stored music in mobile players, the digital signal predistortion can be used before the analog output amplification to facilitate working in an energy-saving but non-linear region of the amplification.

Figure 1:
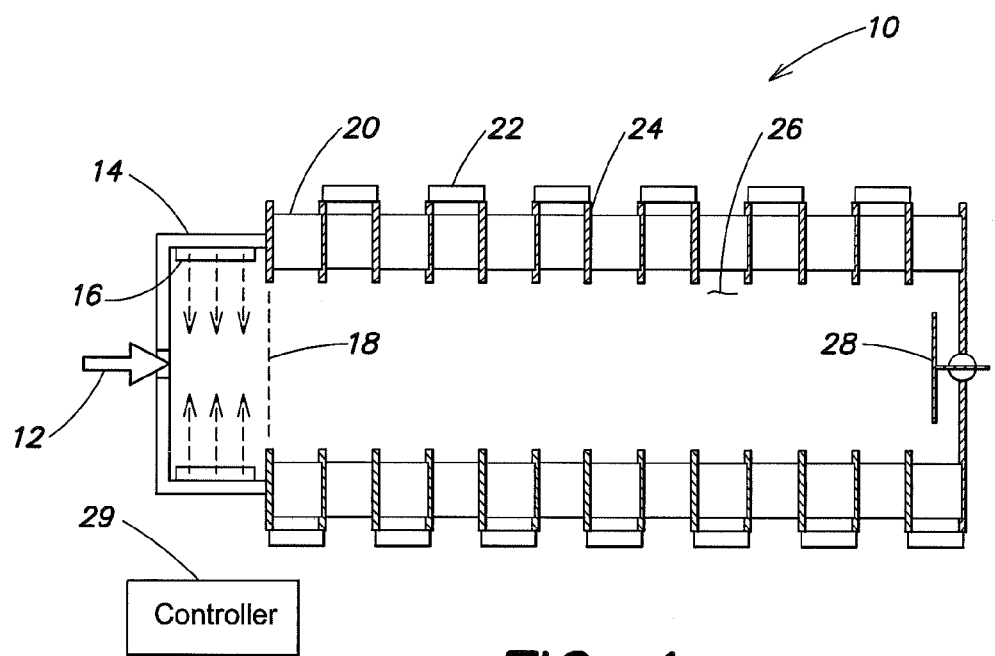
FIG. 1 illustrates a portion of an ion mobility spectrometer 10.

One technique for measuring ion mobility spectra may be performed using the commercially available apparatus 10 shown in FIG. 1. For example, referring to FIG. 1, a sample gas 12 flowing through an ion source region and a drift region (not shown) can enter a housing 14 of an ion source. The sample gas 12 includes substances (e.g., trace air pollutants) for analysis such as molecules of explosives, traces of drugs, etc. The nitrogen and oxygen ions generated by electrons from a beta emitter 16, for example $^{63}$Ni, or by highly accelerated electrons produced by X-rays, react in complex reactions with water molecules to form reactant ions. The reactant ions react by protonation or deprotonation with the molecules of the sample gas. A slight gas flow (or a moderate electric field) moves the ions and the remaining reactant ions towards a modulating gating grid 18 to which a modulation control voltage is applied. In one embodiment, the ion beam has a diameter of approximately 5 millimeters. The broad ion beam passes through the gating grid 18. The modulation control voltage may be applied to the wires of the gating grid 18 in a bipolar manner, i.e. with two phases. Alternatively, some of the wires can have a constant potential, where a single-phase modulation control voltage is applied to the other wires.

In conventional pulse mode, the gating grid 18 transmits the ion flow or blocks it, and therefore generates ion current pulses with pulse lengths of between, for example, 150 and 300 microseconds. In one embodiment, the gating grid 18 is a transparent Bradbury-Nielsen grid of closely neighboring pole wires placed at different spatially alternating potentials. The ions are attracted to the wires of appropriate polarity and are discharged, thereby blocking the ion current. Where the voltage differences at the wires are set to zero, the gating grid 18 is switched to a transmission mode, and the ions pass the grid and enter the drift region 26. The ions are then pulled through the drift region by the electric field. The electric field is generated by electrodes 24, which are supplied with corresponding potentials by a chain of resistors 22. The electrodes 24 are separated by ceramic insulators 20. The drift region 26 typically has a slight opposing gas stream. This opposing gas stream however typically does not affect the measurements because it has a relatively slow speed as compared to the drift speed.

The ion packets directed into the drift region 26 via pulses according to the conventional operating mode drift with their characteristic speed through the drift tube, which is about, for example, 10 centimeters long for trace pollutant detectors, to an ion detector 28. The ion detector 28 measures the ions as ion currents. The ion detector 28 is constructed as a flat collector plate to prevent time smearing, and functions as a Faraday collector. A screen grid may be inserted in front of the collector plate as a shield against the inductive effect of the moving ions. The ion current measured at the detector 28 is amplified, digitized and electronically stored as digitized ion current values.

The ions are transmitted by the gating grid 18 during the pulse mode for a relatively short duration of between, for example, about 150 and 300 microseconds. The complete mobility spectrum is directly measured at the detector 28 for a duration of, for example, about 30 ms. To improve the signal-to-noise ratio, the process is repeated, for example 30 times, and the spectra obtained are summed to provide a total measurement time of approximately one second for 30 repetitions.

Figure 2:
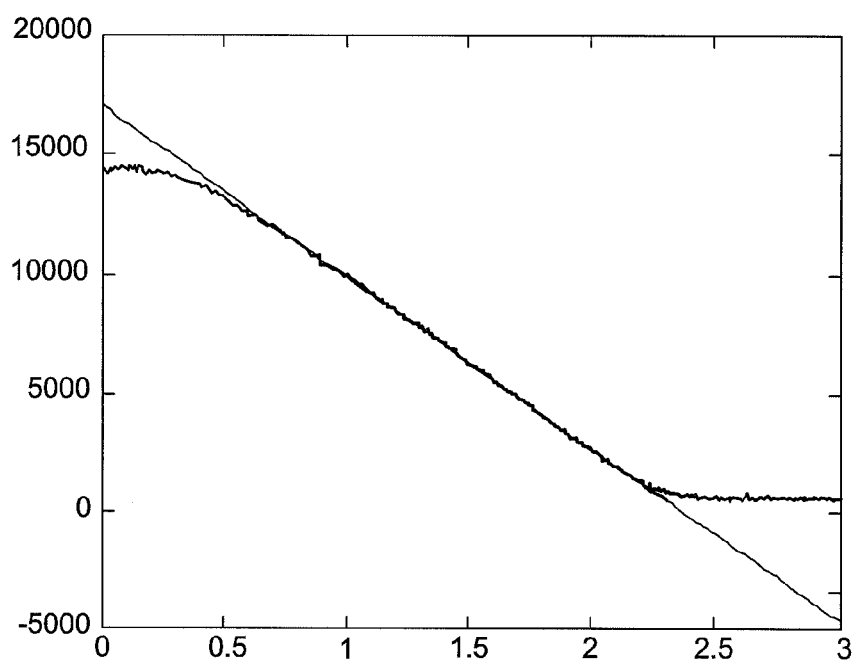
FIG. 2 graphically illustrates a measured transmission characteristic of a gating grid for an ion current in picoamperes (ordinate) as a function of a control voltage in volts (abscissa)

A conventional gating grid is operated in square-wave mode with the two switching states "on" and "off". In contrast, according to an aspect of the present invention, the gating grid 18 applies an analog modulation to the ion current via a continuously varying control voltage, which follows a modulation function. A controller 29 controls the application of the continuously varying control voltage for the gating grid 18 to achieve the analog modulations, and processes the detected current signal to obtain the mobility spectrum. The modulation of the ion current should range from zero to the full ion current, where possible, such that substantially all the ions participate in the coding and decoding. This can be accomplished using, for example, a conventional gating grid 18 that switches between two binary limiting states. FIG. 2 shows that the gating grid has a largely linear characteristic for analog control, but has two transition curves in the vicinity of complete blockage and complete opening which are almost symmetrical to each other.

Figure 3:
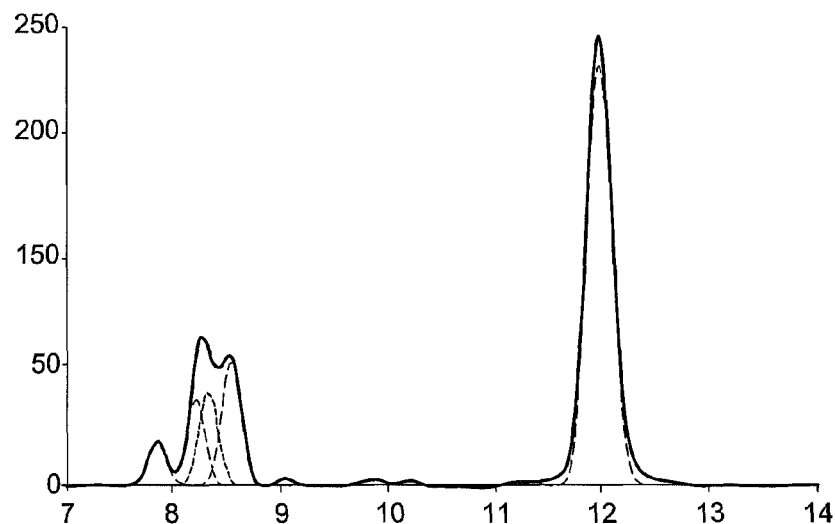
FIG. 3 exhibits an ion mobility spectrum produced by a linear chirp with a duration of one second.
Figure 4:
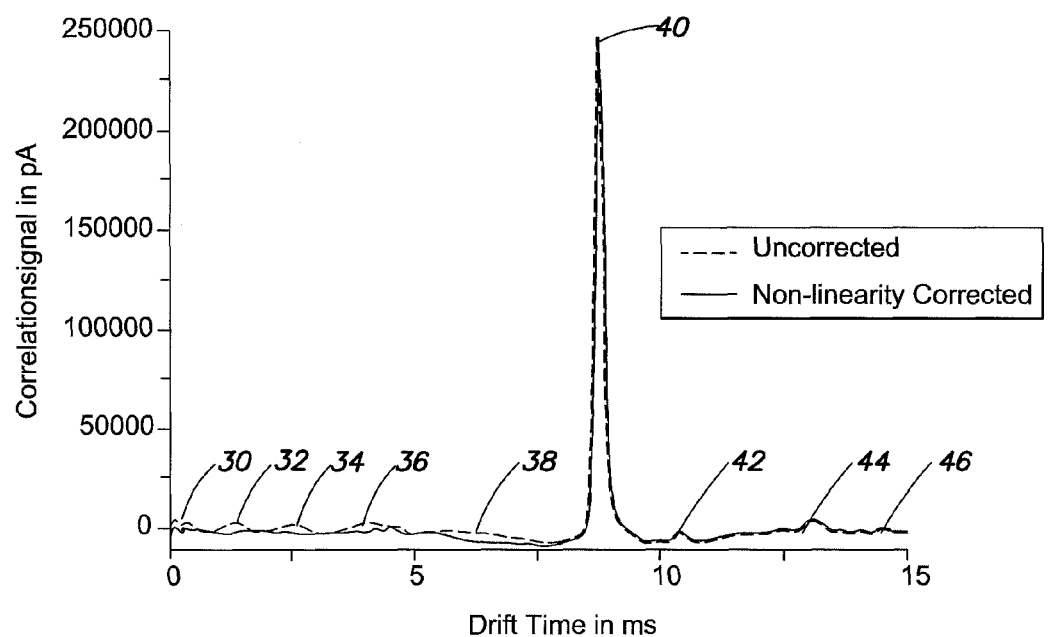
FIG. 4 illustrates two ion mobility spectra of a substance with a peak, both ion mobility spectra obtained with a short scanning time of one tenth of a second.

The analog modulation may be performed using the gating grid 18 as the modulator, where a continuous modulation function with an instantaneous frequency varying over a wide frequency range is used, and where the resulting ion current signal is decoded at the detector by a correlation with the modulation function. For long measuring times of one or more seconds, relatively good mobility spectra can be produced without predistortions of the modulation function. Such a mobility spectrum is shown in FIG. 3. This mobility spectrum exhibits a relatively good signal-to-noise ratio. The substantially noiseless signals make it possible to separate even superimpositions of small peaks. The mobility spectrum, which was generated by a linear chirp having a duration of approximately one second, can therefore be evaluated.

Where the measuring time is shortened, for example, to one tenth of a second, side bands of strong peaks appear as is shown by the mobility spectrum represented by the dashed line of FIG. 4. FIG. 4 illustrates two ion mobility spectra of a substance with a peak 40, obtained with a short scanning time of one tenth of a second. The uncorrected spectrum (dashed line) shows the side bands 30-38, which are no longer present in the corrected spectrum (straight line) obtained by application of the predistorted modulation function. The peaks 42-46 correspond to the signals of real ions of different mobilities. The abscissa presents the drift times in milliseconds. Notably, the distortion of the chirp amplitudes removes the side bands in a mobility spectrum generated by the chirp using the ion mobility spectrometer 10 with the gating grid 18. The obtained mobility spectrum therefore has a smooth background characteristic on both sides of the intense mobility signal, even for short measuring times of, for example, a tenth of a second. This in turn permits the mobility spectrum to be evaluated using conventional methods. The mobility spectrum provides a high mobility resolution and a signal-to-noise ratio which may be more than five times higher than a signal-to-noise ratio provided by conventional operation with ion current pulses.

As set forth above, inclusion of side bands with short measuring times can be detrimental since the evaluation of dynamic processes requires a series of mobility spectra in rapid succession. Explosive and drug detection at an airport typically uses short measuring times for the dynamic tracing of the signals. The temporal characteristic of the ratios of different ions with respect to one another using this inventive method, however, gives the identification of the substances such a high degree of certainty that the rate of false alarms is strongly reduced.

Mathematical simulations have shown that the side bands are generated by the nonlinear grid modulations. Distortions caused by the transition curves close to the complete closing or opening of the modulator have little effect as long as they are ideally symmetrical and do not substantially interfere with the alternating characteristic of the modulation. Asymmetries of the transition curves or a slight curvature in the linear part of the transmission curve, on the other hand, produce asymmetric modulations, which produce the side bands.

The inventive method compensates at least the asymmetric parts of the distortion of the modulators (the gating grids 18) with a corresponding predistortion such that a modulated ion current which is symmetric about its average value is generated by the modulation.

Where the central region of the transmission curve, which ideally should be straight, has a quadratic term with a slightly parabolic curvature, a predistortion of the modulation function $f(t)$ is superimposed with a quadratic part $f^2(t)$ to compensate for the distortion by the parabolic curvature. Where a linear chirp of the form $f(t)=a+b \sin(\pi v\, t^2/T)$ is used, for example, a predistorted modulation function $f^*(t)=A+B \sin(\pi v\, t^2/T)+C \sin^2(\pi v\, t^2/T)$ with suitable coefficients A, B and C can compensate the parabolic curvature of the transmission curve.

Generally, the modulation function $f(t)$ with contributions of higher powers $f^2(t)$, $f^3(t)$, $f^4(t)$ etc. can be superimposed in order to counteract the distortion of the modulator.

In order to continuously modulate the ion current with a chirp-like function having instantaneous frequency that varies over a wide frequency range, it is expedient to initially calculate the modulation function as a series of digital values, and then store these values for later use. During the modulation, the series of values is fed to a digital-to-analog converter (DAC), which has a voltage output connected to the modulator. The ion current signal at the detector is digitized and stored as a sequence of digital ion current values. The correlation of both digital value sequences of values results in the mobility spectrum.

In some embodiments, the modulation function is digitally predistorted by calculating an additional sequence of digital values representing the distorted modulation function and storing the values of the distorted modulation function as an additional sequence of digital values. This computational solution does not require additional modifications to the instruments. Rather, the output voltage of the DAC can also be analog distorted in an electronic circuit before being fed to the modulator as the control voltage.

The ion current signal can be decoded with the undistorted modulation function, because the distortion has been almost completely removed by the predistorted modulation. It is therefore expedient to keep the sequence of undistorted values of the modulation function stored. It is also possible to decode the signal using the distorted modulation function with slightly deteriorated result. This therefore obviates the need to store two sequences of values.

As set forth above in reference to U.S. 2009/0236514, the ion current signal and the modulation function can be correlated either by an electronic correlator, using the analog ion current signal, or by a suitable computer program, using the digital ion current signal. This requires that the modulation function possesses a well-localized auto-correlation function. According to the so-called "matched filter" theory, correlating the measured signal with the modulation signal produces the best signal-to-noise ratio in the ideal case; i.e. without diffusion losses. The mobility spectrum is determined from the correlation of the ion current signal and the modulation function, and can be provided as either an analog spectrum or a digital spectrum. To evaluate it further in a computer, the analog mobility spectrum should be digitized.

The mobility spectra have a relatively high resolution that is substantially noise free. The mobility spectrum includes substantially no side bands even, for example, in short measuring times of far below one second. A Gaussian curve therefore can be easily fit to the mobility spectrum, even for small signals close to the detection limit. The analog modulation permits the correlation analysis to operate stably, quite unlike a square-wave modulation function.

Although the present invention has been illustrated and described with respect to several preferred embodiments thereof, various changes, omissions and additions to the form and detail thereof, may be made therein, without departing from the spirit and scope of the invention.

What is claimed is:

1. A method for measuring mobility spectrum of ions in an ion mobility spectrometer having an ion source, a modulator, an ion drift region and an ion detector disposed at the end of the ion drift region, the method comprising:
   modulating an ion current of the ion source with the modulator by varying an instantaneous frequency of a continuous modulation function across a frequency range; and
   measuring the mobility spectrum by correlating the ion current measured at the detector and the modulation function;
   where a predistortion of the continuous modulation function substantially compensates for a distortion created by the modulator.

2. The method of claim 1, where at least asymmetric portions of the distortion are compensated by the predistortion of the continuous modulation function.

3. The method of claim 1, where the predistortion of the continuous modulation function includes superimpositions with contributions of higher powers of the continuous modulation function.

4. The method of claim 1, where the continuous modulation function is a substantially linear chirp defined as $f(t)=a+b \sin(\pi v\, t^2/T)$, and where the predistorted continuous modulation function is defined as $f^*(t)=A+B \sin(\pi v\, t^2/T)+C \sin^2(\pi v\, t^2/T)$.

5. The method of claim 1, where the continuous modulation function is digitally predistorted.

6. The method of claim 1, where the continuous modulation function is analogly predistorted via an electric circuit.

7. The method of claim 1, further comprising decoding the measured ion current by correlating ion current values of the measured ion current with the continuous modulation function.

8. The method of claim 1, further comprising decoding the measured ion current by correlating ion current values of the measured ion current with the predistorted continuous modulation function.

9. The method of claim 1, where the modulator comprises a bipolar gating grid.

10. The method of claim 1, where the instantaneous frequency ranges between a lower frequency limit and an upper frequency limit selected according to resolution requirements.

11. The method of claim 1, further comprising extending the predistortion of the continuous modulation function over a measuring period.

* * * * *